US008623935B2

(12) United States Patent
Hobbs et al.

(10) Patent No.: US 8,623,935 B2
(45) Date of Patent: Jan. 7, 2014

(54) ANTIMICROBIAL COMPOSITIONS

(75) Inventors: Terry R. Hobbs, St Paul, MN (US);
Robert A. Asmus, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 207 days.

(21) Appl. No.: 12/811,184

(22) PCT Filed: Dec. 31, 2008

(86) PCT No.: PCT/US2008/088590
§ 371 (c)(1),
(2), (4) Date: Jun. 29, 2010

(87) PCT Pub. No.: WO2009/088894
PCT Pub. Date: Jul. 16, 2009

(65) Prior Publication Data
US 2010/0282409 A1    Nov. 11, 2010

Related U.S. Application Data

(60) Provisional application No. 61/018,165, filed on Dec. 31, 2007.

(51) Int. Cl.
*C08K 5/00* (2006.01)
*C08K 5/05* (2006.01)

(52) U.S. Cl.
USPC ............................. 523/122; 524/284; 524/379

(58) Field of Classification Search
USPC .................................. 523/122; 524/284, 379
See application file for complete search history.

(56) References Cited

U.S. PATENT DOCUMENTS

| | | |
|---|---|---|
| 4,010,252 A | 3/1977 | Hewitt |
| 4,485,029 A | 11/1984 | Kato et al. |
| 4,542,012 A | 9/1985 | Dell |
| 4,584,192 A | 4/1986 | Dell et al. |
| 4,666,896 A | 5/1987 | Warner et al. |
| 4,981,678 A | 1/1991 | Tomlinson |
| 5,017,617 A | 5/1991 | Kihara et al. |
| 5,208,257 A | 5/1993 | Kabara |
| 5,547,662 A | 8/1996 | Khan et al. |
| 5,547,677 A | 8/1996 | Wright |
| 5,549,901 A | 8/1996 | Wright |
| 5,629,006 A | 5/1997 | Hoang et al. |
| 5,708,023 A | 1/1998 | Modak et al. |
| 5,776,430 A | 7/1998 | Osborne et al. |
| 5,830,488 A | 11/1998 | Asaka |
| 5,951,993 A | 9/1999 | Scholz et al. |
| 5,965,088 A | 10/1999 | Lever et al. |
| 5,965,610 A | 10/1999 | Modak et al. |
| 6,022,551 A | 2/2000 | Jampani et al. |
| 6,121,327 A | 9/2000 | Tsuzuki et al. |
| 6,162,447 A | 12/2000 | Fankhauser et al. |
| 6,187,327 B1 | 2/2001 | Stack |
| 6,211,243 B1 | 4/2001 | Johnson |
| 6,338,855 B1 * | 1/2002 | Albacarys et al. ............ 424/409 |
| 6,559,189 B2 | 5/2003 | Baker, Jr. et al. |
| 6,582,711 B1 | 6/2003 | Asmus et al. |
| 6,605,666 B1 | 8/2003 | Scholz et al. |
| 6,635,676 B2 | 10/2003 | Baker et al. |
| 6,723,689 B1 | 4/2004 | Hoang et al. |
| 6,838,078 B2 | 1/2005 | Wang et al. |
| 6,951,642 B2 | 10/2005 | Scholz et al. |
| 7,030,203 B2 | 4/2006 | Mosbey et al. |
| 7,147,873 B2 | 12/2006 | Scholz et al. |
| 7,323,163 B2 | 1/2008 | Wang et al. |
| 2002/0013305 A1 | 1/2002 | Hanna |
| 2002/0037268 A1 | 3/2002 | Stack |
| 2002/0058010 A1 | 5/2002 | Picard-Lesboueyries |
| 2004/0091428 A1 | 5/2004 | Libin |
| 2004/0186183 A1 | 9/2004 | Johnson |
| 2004/0191274 A1 | 9/2004 | Grayson et al. |
| 2004/0247685 A1 | 12/2004 | Modak et al. |
| 2005/0058673 A1 | 3/2005 | Scholz et al. |
| 2005/0084471 A1 | 4/2005 | Andrews et al. |
| 2005/0089539 A1 | 4/2005 | Scholz et al. |
| 2005/0123590 A1 | 6/2005 | Burton et al. |
| 2006/0018847 A1 | 1/2006 | Kroepke et al. |
| 2006/0029569 A1 | 2/2006 | Scholz et al. |
| 2006/0034798 A1 | 2/2006 | Mosbey et al. |
| 2006/0051384 A1 | 3/2006 | Scholz et al. |
| 2006/0051385 A1 | 3/2006 | Scholz |

(Continued)

FOREIGN PATENT DOCUMENTS

| | | |
|---|---|---|
| EP | 0 172 724 | 2/1986 |
| EP | 0 244 144 | 11/1987 |

(Continued)

OTHER PUBLICATIONS

Block, S., "Acid-Anionic Surfactant Sanitizers", Disinfection, Sterilization and Preservation, Chapter 16, Lea & Febiger, Philidelphia PA, pp. 319-323 (1977).

*Primary Examiner* — Kriellion Sanders

(57) ABSTRACT

Antimicrobial compositions are provided that include a hydroalcoholic solvent system comprising a lower $C_2$-$C_5$ alcohol and water; a cationic antimicrobial agent such as chlorhexidine gluconate; a hydrophobic polymer soluble in the lower alcohol; an emollient ester such as diesters of bibasic acids and triesters of citric acid; and an optional fatty component containing at least one free hydroxyl group, such as a $C_{12}$-$C_{21}$ fatty alcohol, a $C_{12}$-$C_{21}$ fatty ester, a $C_{12}$-$C_{21}$ fatty ether, a $C_{12}$-$C_{21}$ fatty amide, and combinations thereof. The compositions described herein display improved antimicrobial efficacy and improved cosmetic elegance.

18 Claims, No Drawings

(56) References Cited

U.S. PATENT DOCUMENTS

| | | | |
|---|---|---|---|
| 2006/0052452 A1 | 3/2006 | Scholz | |
| 2006/0099237 A1 | 5/2006 | Modak et al. | |
| 2009/0226541 A1* | 9/2009 | Scholz et al. | 424/672 |

FOREIGN PATENT DOCUMENTS

| | | |
|---|---|---|
| EP | 0375827 | 7/1990 |
| EP | 0 937 812 | 8/1999 |
| EP | 1 990 050 A1 | 11/2008 |
| GB | 2 193 892 | 2/1988 |
| GB | 2 338 649 | 12/1999 |
| JP | 63-0166837 | 2/1987 |
| JP | 63-130541 | 6/1988 |
| JP | 8-151326 | 11/1994 |
| JP | 9-510976 | 11/1997 |
| JP | 11349418 | 12/1999 |
| JP | 2002-145736 | 5/2002 |
| WO | WO 85/01876 | 5/1985 |
| WO | WO 94/27440 | 12/1994 |
| WO | WO 95-26134 | 10/1995 |
| WO | WO 95/31956 | 11/1995 |
| WO | WO 96/29867 | 10/1996 |
| WO | WO 97/00076 | 1/1997 |
| WO | WO 97/16168 | 5/1997 |
| WO | WO 98/30095 | 7/1998 |
| WO | WO 98/56253 | 12/1998 |
| WO | WO 99/22703 | 5/1999 |
| WO | WO 00/71183 | 11/2000 |
| WO | WO 02/089849 | 11/2002 |
| WO | WO 03/028767 | 4/2003 |
| WO | WO 03-032948 | 4/2003 |
| WO | WO 2004-052308 | 6/2004 |
| WO | WO 2005/023233 | 3/2005 |
| WO | WO 2006/029351 | 3/2006 |
| WO | WO 2008/057773 A2 | 5/2008 |

* cited by examiner

ANTIMICROBIAL COMPOSITIONS

CROSS REFERENCE TO RELATED APPLICATIONS

This application is the National Stage filing under 35 U.S.C. 371 of International Application No. PCT/US2008/088590, filed Dec. 31, 2008, which claims priority to U.S. Provisional Application Ser. No. 61/018,165, filed Dec. 31, 2007, which is incorporated herein by reference.

BACKGROUND

It is a standard practice in the industrialized world to disinfect the skin prior to any invasive procedure such as surgery, catheterization, or needle puncture to reduce the risk of infection. Currently, chlorhexidine compositions are an agent of choice for disinfecting hands, skin, surgical sites, catheter sites, and oral cavities. Chlorhexidine and its salts are well-known antimicrobials with excellent efficacy that are safe to use. Chlorhexidine and its salts also show persistent antimicrobial activity on the skin often for more than 24 hours.

Two hydroalcoholic compositions containing chlorhexidine are currently available. AVAGARD surgical hand prep is a hydroalcoholic composition containing 1% chlorhexidine gluconate in 61% ethanol available from 3M Company. CHLOROPREP surgical prep is a composition containing 2% w/v chlorhexidine gluconate (CHG), 70% v/v isopropanol, and water available from Cardinal Health.

Products that contain chlorhexidine or its derivatives suffer from several disadvantages. Chlorhexidine is a cationic biguanide, which can be readily deactivated by salts (chlorides, carbonates, and the like), nonionic surfactants, anionic surfactants, and anionic compounds such as organic acids or salts of organic acids. Many soaps and skin creams contain these agents and readily deactivate chlorhexidine and its salts.

Chlorhexidine compositions can also be irritating to skin and mucous membranes. Products that contain greater than 2% CHG can cause significant irritation, particularly after repeated use.

Surgical preps containing chlorhexidine and/or other antimicrobials can undermine the adhesion of medical tapes, dressings, and surgical drapes, particularly under wet skin conditions. Chlorhexidine salts in particular exacerbate this problem because they are hydrophilic and remain on the surface of the skin after topical application. Under wet conditions, such as in surgery when large amounts of body fluids or saline are present, the chlorhexidine salts can cause the loss of adhesion of surgical drapes and dressings. This adhesion loss is often called "drape lift" and is highly undesirable because it can interrupt the sterile field, which increases the probability of a surgical site infection.

There is a clear need for chlorhexidine compositions which have low irritation, cosmetic acceptability, excellent efficacy, and improved wet adhesion for use in surgical and catheter sites.

SUMMARY OF THE INVENTION

The present invention provides compositions useful as products for skin disinfection such as skin antiseptics, preoperative surgical preps, hand sanitizers, catheter and i.v. skin preps, and waterless hand scrubs. The preferred formulations of the present invention, in general, have a desirable cosmetic feel after both single and multiple applications. Additionally, preferred formulations maintain or improve adhesion of medical articles to skin, particularly in the presence of moisture. When used as a preoperative surgical prep or antiseptic, the compositions described herein achieve improved antimicrobial efficacy.

In one aspect, an antimicrobial composition is provided, comprising a $C_2$-$C_5$ lower alcohol present in an amount of at least 35 wt-%; a hydrophobic polymer soluble or dispersible in the lower alcohol; an emollient ester; and a cationic antimicrobial agent. The antimicrobial composition is free of surfactants with an HLB greater than 6; and is essentially free of hydrophilic polymers.

In another aspect, an antimicrobial composition is provided, comprising a $C_2$-$C_5$ lower alcohol present in an amount of at least 35 wt-%; a hydrophobic polymer soluble in the lower alcohol; a cationic antimicrobial agent; and an emollient ester selected from the group consisting of diesters of bibasic acids, triesters of citric acid, diesters of diols, triesters of triols, and combinations thereof. The antimicrobial composition is free of surfactants with an HLB greater than 6; and is essentially free of hydrophilic polymers.

In another aspect, an antimicrobial composition is provided, comprising a $C_2$-$C_5$ lower alcohol present in an amount of at least 35 wt-%; a hydrophobic polymer soluble in the lower alcohol selected from the group consisting of acrylates and its derivatives, cellulose and its derivatives, n-vinyl lactam copolymers and vinyl copolymers, and combinations of two or more of the foregoing; a cationic antimicrobial agent; and an emollient ester. The antimicrobial composition is free of surfactants with an HLB greater than 6; and is essentially free of hydrophilic polymers.

In a further aspect, a nonvolatile antimicrobial composition is provided, comprising a hydrophobic polymer; a cationic antimicrobial agent; and an emollient ester selected from the group consisting of an emollient ester selected from the group consisting of diesters of bibasic acids, triesters of citric acid, diesters of diols, triesters of triols, and combinations thereof. The nonvolatile composition is essentially free of hydrophilic polymers and free of surfactants.

In a further aspect, a method of preventing or treating a skin condition of a mammal, the method comprising the step of applying the antimicrobial compositions of any of compositions above to skin.

In another aspect, a method of preventing surgical site or catheter site infections is provided, the method comprising the step of applying the antimicrobial compositions of any of the compositions above prior to surgery or catheterization.

DEFINITIONS

"Ambient temperature" as used herein refers to the temperature range between about 21° and 25° C.

"Emollient" as used herein refers to materials which are capable of maintaining or improving the moisture level, compliance, or appearance of the skin when used repeatedly. Emollients often act to increase the moisture content of the stratum corneum. Emollients are generally separated into two broad classes based on their function. The first class of emollients function by forming an occlusive barrier, which reduces water evaporation from the stratum corneum. The first class of emollients is further subdivided into compounds, which are waxes at room temperature and compounds which are liquid or oils. The second class of emollients penetrate into the stratum corneum and physically bind water to prevent evaporation. The second class of emollients includes those that are water soluble and are often referred to as humectants. For the purposes of this invention, the emollient esters are considered separate and distinct from any other emollients which may be used, even though the emollient esters may function as occlusive emollients and aid in maintaining or improving the skin condition.

"Polymer" as used herein refers to a natural or synthetic molecule having repetitive units and a number average molecular weight of at least 10,000, and includes homopolymers and copolymers of any length.

"(Meth)acrylate monomers" are acrylic acid esters or methacrylic acid esters of alcohols.

"Copolymer" includes a polymer of any length (including oligomers) of two or more types of polymerizable monomers, and therefore includes terpolymers, tetrapolymers, etc., which can include random copolymers, block copolymers, or sequential copolymers.

"Lotion" means liquid or cream, free of any propellant.

"Solvent system" or "hydroalcoholic solvent system" as used herein refer to the combination of the lower ($C_2$-$C_5$) alcohol and water in the compositions described herein.

"Solvent" as used herein refers to any organic compound used to dissolve or disperse another compound.

"Surfactant" as used herein is synonymous with "emulsifier," and means an amphiphile (a molecule possessing both polar and nonpolar regions which are covalently bound) capable of reducing the surface tension of water and/or the interfacial tension between water and an immiscible liquid.

"Fatty" as used herein refers to a hydrocarbon chain length of 8 or more carbon atoms (odd or even number), unless otherwise specified.

"Cidatrope" as used herein is a term for a hydrophobic component in the composition that enhances the effectiveness of the antimicrobial composition such that when the composition less the antimicrobial agent and the composition less the cidatrope component are used separately, they do not provide the same level of antimicrobial activity as the composition as a whole. For example, a cidatrope component in the absence of the antimicrobial agent may not provide any appreciable antimicrobial activity. The enhancing effect can be with respect to the level of kill, the speed of kill, and/or the spectrum of microorganisms killed, and may not be seen for all microorganisms. The cidatrope component may be a synergist such that when combined with the remainder of the composition, the composition as a whole displays an activity that is greater than the sum of the activity of the composition less the cidatrope component and the composition less the antimicrobial agent. The cidatrope preferably is a liquid at ambient conditions with a melt temperature less than 25° C. When more than one cidatrope is present in the antimicrobial composition, at least one cidatrope has a melt temperature less than 25° C. The hydrophobic polymer, the emollient esters, and the optional fatty component all function as cidatropes in the compositions described herein.

"Hydrophobic" or "water insoluble" refers to a material that will not significantly dissolve in water at 23° C. Solubility can be determined by thoroughly mixing the compound with water at the appropriate concentration at 23° C. for at least 24 hours (or at elevated temperature if that is necessary to dissolve the compound), allowing this to sit at 23-25° C. for 24 hours, and observing the sample. In a glass jar with a 4-cm path length the sample should have evidence of a second phase, which can be liquid or solid and may be separated on the top, bottom, or distributed throughout the sample. For crystalline compounds care should be taken to avoid producing a supersaturated solution. The components should be mixed and observed. Cloudiness or presence of a visible precipitate or separate phase indicates that the solubility limit has been exceeded. Typically, when placed in 1×1 cm cell the sample has less than 70% transmission measured in a suitable spectrophotometer at a wavelength of 655 nm. For solubility determinations less than that which can be observed with the naked eye the solubility is determined using radiolabeled compounds as described under "Conventional Solubility Estimations in Solubility of Long-Chain Fatty Acids in Phosphate Buffer at pH 7.4," Henrik Vorum, et al. in *Biochimica et. Biophysica Acta,* 1126, 135-142 (1992). The hydrophobic polymers of this invention have a solubility in water of less than 1%, more preferably less than 0.5%, even more preferably less than 0.25%, and most preferably less than 0.10%.

"Hydrophilic" or "water soluble" or "water swellable" refers to a material that will dissolve, solubilize, disperse or otherwise suspend in water (or other aqueous solution as specified) at a temperature of 23° C. in an amount of at least 7% by weight, preferably at least 10% by weight, more preferably at least 20% by weight, even more preferably at least 25% by weight, even more preferably at least 30% by weight, and most preferably at least 40% by weight, based on the total weight of the hydrophilic material and the water. The component is considered dissolved if after thoroughly mixing the compound with water at 60° C. for at least 4 hours and allowing this to cool to 23-25° C. for 24 hours, and mixing the composition thoroughly it appears uniform clear solution without visible cloudiness, phase separation, or precipitate in a jar having a path length of 4 cm. Typically, when placed in 1×1 cm cell, the sample exhibits greater than 70% transmission measured in a suitable spectrophotometer at a wavelength of 655 nm. Water dispersible hydrophilic materials disperse in water to form uniform cloudy dispersions after vigorous shaking of a 5% by weight mixture of the hydrophilic component in water. Water swellable hydrophilic materials solubilize or suspend in water, including those materials that form of a viscous solution or viscous gel.

"Nonvolatile" means that the component does not evaporate readily at ambient conditions, such that a 20 gm sample in a 4 $cm^2$ dish does not lose more than 2% of its weight, e.g., within 60 minutes upon exposure to ambient conditions. Examples of nonvolatile components of the compositions described herein include glycerin, chlorhexidine and its salts, and fatty components with a chain length greater than 10 carbons.

"Essentially free" means less than 1% by weight, more preferably less than 0.5% by weight, and even more preferably less than 0.1% by weight, of a component based on the total weight of the composition.

DESCRIPTION OF THE PREFERRED EMBODIMENTS

The compositions provided herein are hydroalcoholic formulations that provide rapid and persistent antimicrobial activity. The compositions include a hydroalcoholic solvent system comprising a lower $C_2$-$C_5$ alcohol and water, and a cationic antimicrobial agent such as chlorhexidine gluconate. The compositions also include a hydrophobic polymer soluble or dispersible in the hydroalcoholic composition, as discussed further below. The compositions also include a hydrophobic emollient ester such as diesters of bibasic acids and triesters of citric acid. The compositions can also include an optional fatty component containing at least one free hydroxyl group, such as a $C_{12}$-$C_{21}$ fatty alcohol, a $C_{12}$-$C_{21}$ fatty ester, a $C_{12}$-$C_{21}$ fatty ether, a $C_{12}$-$C_{21}$ fatty amide, and combinations thereof. The compositions described herein are useful as preoperative surgical preps, hand antiseptics, dental antiseptics and varnishes, antimicrobial swaps, and wipes for skin disinfection. The compositions are particularly useful for preventing surgical site and catheter site infections when used as an antiseptic on the skin.

The compositions described herein display improved antimicrobial efficacy and improved cosmetic elegance. Improved antimicrobial efficacy means a composition that exhibits any one or a combination of the following: (i) the composition maintains antimicrobial activity in the presence of the cationic antimicrobial agent, despite the presence of a component that is known to interact with cationic antimicrobial agent; (ii) the composition improves antimicrobial activity relative to the same composition without one of either the hydrophobic polymer or the emollient ester present; or (iii) the composition with less cationic antimicrobial agent present maintains the same activity relative to a composition with more cationic antimicrobial agent present but lacking one of either the hydrophobic polymer or the emollient ester; or (iv) the composition shows synergistic antimicrobial activity when the cationic antimicrobial agent, hydrophobic polymer and emollient ester are present.

When applied to the skin, the compositions have rapid bactericidal activity due to the high concentration of lower alcohol(s) and the enhanced activity of the cationic antimicrobial agent in the presence of the hydrophobic polymer, the emollient ester, and optionally, the fatty component. After the compositions are applied to the skin, the compositions dry quickly as the lower alcohol evaporates, and a nonvolatile antimicrobial composition remains. This nonvolatile composition comprises the cationic antimicrobial agent, hydrophobic polymer, the emollient ester, and optionally, the fatty component. This antimicrobial composition that remains on the skin is non-irritating and provides persistent bactericidal activity. In addition to enhancing the antimicrobial activity, the hydrophobic polymer can also serve as a protectant and prevent premature removal of the antimicrobial composition by washing off with aqueous fluids.

The compositions described herein also contribute to improved adhesion of medical adhesive articles that may be used in the presence of or on the compositions. Biguanides, such as chlorhexidine gluconate (CHG), are typically water soluble agents, which can resolubilize in the presence of moisture and undermine the skin adhesion of medical adhesive articles such as dressings, adhesive incise drapes or tapes. This loss in adhesion can result in early failure of the medical adhesive article and place the patient at increased risk of infection due to, for example, lift of an incise drape at the incisional area or loss of secural of a catheter. The compositions of this invention contribute to improved adhesive performance of medical adhesive articles primarily as the result of the hydrophobic polymer, and optionally the fatty component, particularly the fatty alcohols, if present. The improvement in adhesion can be an overall increase in adhesive effect, i.e. increased adhesion of the medical adhesive article to skin coated with the antimicrobial compositions described herein. The improvement in adhesion can also be a reduction in the variability of adhesive performance of the medical adhesive article between patients, resulting in a more universally effective attachment of the medical adhesive article in a given patient population. The improvement in adhesion can also be the prevention of drape lift or loss of adhesion in the presence of water or saline. This provides a benefit when the compositions are used as preoperative surgical preps with the presence of large amounts of blood and saline in the area of the incision.

The inventors of this application have surprisingly found that the combination of the hydrophobic polymers and emollient esters enhances the antimicrobial efficacy of cationic antimicrobial agents such as chlorhexidine and its salts, particularly chlorhexidine gluconate. The inventors have also found that the combination of the hydrophobic polymers with the emollient esters further synergistically enhance the activity of the compositions. Thus, the compositions comprise improved efficacy compared to compositions containing cationic antimicrobial agents currently employed in the art.

The hydrophobic polymers and the emollient esters both function to increase hydrophobicity of the composition. The fatty component, when included, can also further increase the hydrophobic nature of the composition. The increased hydrophobicity of the composition, after drying on skin, functions to improve adhesion of medical articles in the presence of moisture. The hydrophobic nature of the compositions also reduces the "wash off" effect of the active cationic agent by hydrophilic or aqueous solutions employed in the healthcare setting such as sterile saline rinses.

Unexpectedly, the hydrophobic polymer in combination with the emollient ester did not adversely affect the antimicrobial activity of the composition, and in most cases, improve the antimicrobial efficacy of the antimicrobial composition. Surprisingly the addition of emollient ester with the hydrophobic polymer dramatically improved the activity despite the obvious dilutive effect of the emollient ester, for example, adding an additional 3.5% solids of emollient to the dried composition diluted the dried matrix from 22% CHG (4.5:1) to 12.5% CHG (8:1). This is surprising for several reasons. First, the dilution effect of the hydrophobic polymer and the emollient ester on the cationic antimicrobial agent does not affect the antimicrobial activity of the composition. Thus, lower levels of cationic antimicrobial agent, particularly CHG, are necessary to produce a given antimicrobial efficacy level. This reduction in concentration of the cationic antimicrobial agent on the skin can also aid in reducing the skin irritation possible with compositions containing high concentrations of CHG. When compositions containing only alcohol, CHG, and water are applied to the skin, the alcohol quickly evaporates off essentially leaving behind a film with a high concentration of CHG, which has the potential to irritate the skin.

Conversely, the increased hydrophobicity due to the hydrophobic polymer and emollient ester, and the fatty component when used, also allows for increased levels of CHG in compositions, which increases the antimicrobial activity of the compositions and maintains desirable cosmetic feel while minimizing skin irritation.

Second, when used with chlorhexidine salts, the inventors also found surprising that the combination of the hydrophobic polymer and emollient ester enhanced antimicrobial efficacy. Most emollients such as nonionic surfactants or higher alcohols are likely to decrease chlorhexidine activity, as discussed in U.S. Pat. No. 5,017,617. Anionic surfactants are generally incompatible and may reduce the antimicrobial activity of chlorhexidine salts. The use of nonionic surfactants can also have a dramatic effect on the availability of chlorhexidine salts and their activity. While not wanting to be bound by theory, one explanation may be micellular binding of the chlorhexidine.

An optimal range of antimicrobial efficacy occurs with increasing addition of the hydrophobic polymers and the emollient ester. At higher levels of the hydrophobic polymer combined with the emollient ester, a gradual reduction in antimicrobial efficacy occurs, most likely due to the dilution effect that eventually overwhelms the cationic antimicrobial agent. In a preferred embodiment, the ratio of nonvolatile hydrophobic components (e.g., the total of the hydrophobic polymer, the emollient ester, the optional fatty component, and other lipids, if any) to the cationic antimicrobial agent is at least 0.5:1; more preferably 1:1; even more preferably 2:1, and most preferably 3:1.

For certain embodiments of the antimicrobial composition, the weight ratio of the emollient ester to the cationic antimicrobial agent is at least 0.5:1.

For certain embodiments of the antimicrobial composition, the weight ratio of emollient ester to the cationic antimicrobial agent is at least 1:1.

For certain embodiments of the antimicrobial composition, the weight ratio of the combination of the hydrophobic polymer and the emollient ester to the cationic antimicrobial agent is at least 1:1.

For certain embodiments of the antimicrobial composition, the weight ratio of the combination of the hydrophobic polymer and the emollient ester to the cationic antimicrobial agent is at least 2:1.

The antimicrobial efficacy of the composition remains high at ratios exceeding 6:1 or event 8:1, but the increasing levels of hydrophobic polymer and emollient ester begin to negatively impact both the cosmetic feel of the composition and the time to dry (or at least the appearance of dryness). The emollient esters in particular will contribute an oily look and feel that may be aesthetically undesirable in use.

When applied, the antimicrobial composition is preferably a hydroalcoholic composition in solution form. At a minimum, the cationic antimicrobial agent, the hydrophobic polymer and the emollient ester when used should be soluble at ambient conditions in the lower alcohol and/or the hydroalcoholic solvent system.

Lower Alcohol

The alcohol used in the present invention is a lower hydrocarbon chain alcohol such as a $C_2$-$C_5$ alcohol. In preferred embodiments the alcohol is chosen from ethanol and isopropanol, and most preferably ethanol. Ethanol is a preferred alcohol based on broad spectrum and quick kill of microbes and an odor acceptable to consumers such as doctors, nurses and clinicians. Propyl alcohols (1-propanol and 2-propanol) may also be used.

A blend of two or more lower alcohols may be used as the alcohol content in the hydroalcoholic solvent system. The lower alcohols may be denatured, such as for example, denatured ethanol including SDA-3C (commercially available from Eastman Chemical, Kingsport, Tenn.). Co-solvents may be further included in the composition with the lower alcohol. Considering the topical application contemplated for the antimicrobial composition, suitable co-solvents include acetone, hydrocarbons such as isooctane, glycols, ketones, ethers, and short chain esters.

The $C_2$-$C_5$ lower alcohol used in the compositions is used in sufficient amount to dissolve the hydrophobic polymer and emollient ester. In most embodiments, the lower alcohol is present in an amount of at least 35 wt-%, and even more preferably at least 50 wt-%, based on the total weight of the antimicrobial composition.

Compositions having lower alcohol to water ratios within the range 40:60 to 95:5 ensure an efficacious immediate bacterial kill. In a preferred embodiment the lower alcohol:water ratio is between about 55:45 and 90:10, and more preferably at least 65:35. Higher lower alcohol to water ratios are used in a preferred embodiment for optimum antimicrobial activity and to ensure the composition is fast drying.

A useful concentration of the hydrophobic polymer and the cationic antimicrobial agent depend on their respective solubilities in a given hydroalcoholic solvent system. For example, the solubility of CHG in the hydroalcoholic solvent system decreases with increasing $C_2$-$C_5$ alcohol concentration. In contrast, the hydrophobic polymers may require increased levels of $C_2$-$C_5$ alcohol concentration to solubilize the hydrophobic polymers. One skilled in the art can readily determine an optimum range of concentrations based on the solubility of the cationic antimicrobial agent and the hydrophobic polymer for a given antimicrobial composition or a given solvent system.

Hydrophobic Polymers

The antimicrobial composition includes a hydrophobic polymer soluble in the lower alcohol and with the emollient ester provides improved antimicrobial efficacy to the antimicrobial composition. For certain embodiments, the hydrophobic polymers of this invention have a solubility in water of less than 1%, more preferably less than 0.5%, even more preferably less than 0.25%, and most preferably less than 0.10%. Films formed after drying the antimicrobial composition adhere well to the skin, remain flexible and do not crack when the skin is gently flexed, and do not wash off when exposed to water or body fluids.

The antimicrobial composition can be tested for resistance to water as follows: The composition is applied to the forearms of healthy volunteers. The composition is applied as a uniform wet coating in an amount of approximately 4 milligrams per square centimeter (mg/cm$^2$) and allowed to thoroughly dry (typically a minimum of 5 minutes) over an area of approximately 5×5 cm. The dried composition is exposed to running tap water at a temperature of 23° C.-24° C. and a flow rate of about 2.5 liters/minute (L/min). The water is allowed to hit the arm immediately above the test site and run down over the site. The arm is held at an angle of approximately 45 degrees and the water is allowed to drop from approximately 15 cm before it hits the arm. The time for complete loss of color is recorded. BETADINE Surgical Solution (10% povidone-iodine, "paint") may be used as a control and this typically lasts for less than 5 seconds. Compositions that are not colored may be tested by addition of a suitable colorant. The colorant should not adversely affect the substantivity and thus pigments are often employed. Compositions which when dried are resistant to water resist wash off and in certain embodiments have a substantivity value in excess of 30 seconds, preferably in excess of 60 seconds, more preferably in excess of 90 seconds. For certain embodiments, the substantivity value, which is the time required to wash the composition off, is at least 5 minutes.

Hydrophobic polymers suitable for use in the antimicrobial compositions include film-forming polymers derived from n-vinyl lactam, such as those described in U.S. Pat. Nos. 4,542,012 and 4,584,192; vinyl polymers as described in U.S. Pat. No. 7,030,203; and cellulose, including its derivatives (other than those that are hydrophilic, water soluble or swellable in water), such as ethyl cellulose.

Suitable hydrophobic polymers include film-forming polymers that are the reaction product of a prepolymer having a plurality of isocyanate functionalities, and a polyvinylpyrrolidone polymer. The polyvinylpyrrolidone polymer is a free-radical-polymerization reaction product of at least N-vinylpyrrolidone and a vinyl-functional compound, as further described in U.S. Pat. No. 4,542,012. Other suitable film-forming polymers include film-forming copolymers comprising (i) a monomeric acrylic or methacrylic acid ester of an alkyl alcohol having from 2 to about 14 carbon atoms and containing a single hydroxyl, (ii) a monomeric methacrylic acid ester of an alkyl alcohol having from 1 to 6 carbon atoms and containing a single hydroxyl, and (iii) an N-vinyl lactam, as further described in U.S. Pat. No. 4,584,192.

Other suitable hydrophobic polymers include vinyl polymers, for example, polymers derived from vinyl monomers such as (meth)acrylates, (meth)acrylamides, vinyl ethers, vinyl acetates and their hydrolyzed derivatives, styrenic compounds (i.e., derivatives of styrene), and N-vinyl lactams (including, for example, N-vinylpyrrolidone, N-vinylcaprolactam, and their derivatives). Suitable vinyl polymers are soluble (i.e., form transparent homogenous solutions) or dispersible in the lower alcohol and tend to be insoluble or sparingly soluble in water. Certain vinyl polymers using combinations of three monomers (terpolymers) are also useful.

A preferred class of polymers useful in the antimicrobial compositions described herein include polymers derived from the polymerization of at least one monoethylenically unsaturated alkyl (meth)acrylic monomer, preferably, an alkyl (meth)acrylic acid ester (i.e., an alkyl acrylate or alkyl methacrylate). One preferred class of vinyl polymers contains at least one copolymerized monoethylenically unsaturated alkyl (meth)acrylic monomer. As used herein, the "monoethylenically unsaturated" term in the alkyl (meth)acrylic monomer refers to the acrylic unsaturation. Preferably, "alkyl (meth)acrylic" monomers include (meth)acrylamides (e.g., octylacrylamide), (meth)acrylates, and combinations thereof. More preferably, the alkyl (meth)acrylic monomer is an alkyl (meth)acrylic acid ester (i.e., an alkyl acrylate or alkyl methacrylate), wherein the alkyl group has at least 4 carbon atoms (on average).

Examples of monomers which may be used to make the hydrophobic polymer include but are not limited to: vinyl pyridine, methyl acrylate, ethyl acrylate, butyl acrylate, ethylhexyl acrylate, isooctyl acrylate, isoamyl acrylate, isobornyl acrylate, isotetradecyl acrylate, lauryl acrylate, stearyl acrylate, behenyl acrylate, ethyl hexyl diglycol acrylate, 2-hydroxy-3-phenoxypropyl acrylate, hydroxybutyl acrylate, hydroxyethyl acrylate, hydroxypropyl acrylate, butoxyethyl acrylate, ethoxy diethyleneglycol acrylate, hexyl polyethyleneglycol acrylate, methoxy triethyleneglycol acrylate, phenoxyethyl acrylate, phenoxy polyethyleneglycol acrylate, tetrahydrofurfuryl acrylate, glycidyl methacrylate, trimethylpropane benzoate acrylate, methyl methacrylate, ethyl methacrylate, butyl methacrylate, octadecyl acrylate, hydroxypropyl methacrylate, hydroxyethyl methacrylate, vinyl acetate, N-vinylpyrrolidone, N-vinyllactams, styrene, styrene macromer, vinyl butyral, acrylamide, dimethylaminoethyl methacrylate, dimethylamino ethylacrylate, diethylamino ethylstyrene, diethylaminoethyl methacrylate, butylaminoethyl methacrylate, aminoethyl methacrylate hydrochloride, diisopropylaminoethyl methacrylate, morpholinoethyl acrylate, morpholinoethyl methacrylate, dimethylaminoneopentyl acrylate, diallylamine, aminoethyl methacrylamide, aminopropyl methacrylamide, dimethylaminopropyl acrylamide, dimethylaminopropyl methacrylamide, dimethylaminoethyl acrylate, dimethylaminoethyl methacrylamide, and their quaternary salts such as dimethylaminoethyl acrylate methylchloride, diallyldimethylammonium chloride, aminopropyl methacrylamide hydrochloride, aminoethyl methacrylamide hydrochloride. The hydrophobic polymer derived from the polymerization of at least one of these monomers may be a homopolymer, copolymer, terpolymer, or a blend of polymers.

Other suitable hydrophobic polymers include cellulose and its hydrophobic derivatives, for example, methyl, ethyl, propyl, and butyl, optionally including hydroxyl, methoxy, ethoxy, propoxy, and butoxy groups, as well as $C_5$-$C_{20}$ alkyl derivatives and derivatives which are a combination thereof. Some examples of such cellulose derivatives include methylhydroxypropylcellulose, cetylhydroxyethylcellulose, hydroxypropylcellulose, ethylhydroxyethylcellulose, ethylcellulose, hydroxymethylcellulose and hydroxybutylmethylcellulose. In a preferred embodiment, the cellulose derivative is ethyl cellulose.

Hydrophobic polymers useful in the antimicrobial compositions described herein are soluble in the hydroalcoholic solvent system, and particularly the lower alcohol. In general, the hydrophobic polymers used herein are insoluble or only sparingly soluble in water. When used alone, the hydrophobic polymers can be capable of forming water-resistant films. Such polymers are desirable in the antimicrobial compositions described herein because they would produce surgical hand preparations and antimicrobial hand lotions, for example, that cannot be easily washed off with water after being applied and dried.

The hydrophobic polymer of the composition, along with the emollient ester, and optionally the fatty component, can also contribute to the improved adhesion of medical adhesive articles to the skin, particularly in the presence of moisture or fluids. The hydrophobic polymer is also preferably liquid to improve the overall cosmetic skin feel of the composition as well.

The hydrophobic polymers are preferably not ethoxylated. Ethoxylation affects the moisture sensitivity of the resultant antimicrobial composition, with a resulting decrease in adhesion performance. If any one of the components is ethoxylated, it is preferably no more than one or two moles of ethylene oxide.

When used, the hydrophobic polymer is present in the composition in an amount of at least 0.1 wt-%, more preferably at least 1 wt-%, even more preferably at least 3 wt-%, and most preferably at least 5 wt-% based on the total weight of the antimicrobial composition. In certain embodiments, the hydrophobic polymer is present in amounts of no more than 10 wt-%, and more preferably no more than 6 wt-%. Higher levels can be used depending on the ratio of cationic antimicrobial agent to total nonvolatile components in the antimicrobial composition as discussed above.

Other polymers and additives may be added, however, it is important that the dried composition form a water resistant film as described above.

Emollient Esters

The antimicrobial composition also includes an emollient ester as a cidatrope that provides improved antimicrobial efficacy to the antimicrobial composition. In most embodiments, the emollient ester preferably comprises a total of at least 8 carbon atoms, preferably comprises no more than 20 carbon atoms, and comprises at least two ester linkages.

The emollient esters used in this invention may serve more than one purpose. They may serve to prevent skin irritation and drying, improve the cosmetic feel of the formulation, enhance the antimicrobial activity of the formulation, and moisturize the skin by reducing water transmission. When used at higher concentrations, the emollient esters also enhance the dry adhesion of medical adhesive articles.

The emollient ester is generally a liquid at room temperature and has poor solubility in water, i.e., soluble in water at 23° C. in amounts less than 2 wt-%. Emollient esters suitable for use as a cidatrope in the antimicrobial compositions are selected from diesters of bibasic acids, diesters of diols, triesters of citric acid, triesters of triols, and combinations thereof.

For certain embodiments, the emollient ester is selected from the group consisting of ($C_1$-$C_8$)alkyl alcohol esters of ($C_2$-$C_{12}$)diacids, for example, dibutyl adipate, diisopropyl adipate, diisobutyl adipate, dihexyl adipate, diisopropyl sebacate, and dibutyl sebacate; diesters of butanediol and hexanediol; propylene glycol dicaprylate; ($C_2$-$C_8$)alkyl alcohol di and triesters of citric acid, for example, tributyl citrate; and combinations thereof. Other emollient esters include dialkyl acid esters of diols, triesters of citric acid, and trialkyl acid esters of triols, and dialklyl alcohol esters of other di and tri carboxylic acids.

For certain embodiments, the emollient ester is selected from the group consisting of dialkyl esters of bibasic acids, trialkyl esters of citric acid, dialkyl esters of diols, trialkyl esters of triols, and combinations thereof. Preferred diesters of bibasic acids include dibutyl adipate, diisopropyl adipate, diisobutyl adipate, dihexyl adipate, diisopropyl sebacate, dibutyl sebacate and mixtures thereof. In a similar manner, preferred triesters of citric acid include tributyl citrate. Preferred diesters of diols include esters of butanediol and hexanediol. Diesters of propylene glycol such as propylene glycol dicaprylate may also be useful. The most preferred emollient esters are diisopropyl adipate, dibutyl adipate, and tributyl citrate.

Examples of other emollients that may be suitable include, but are not limited to, short chain (i.e, C1-C6) alkyl or (C6-C12)aryl esters of long (i.e., C8-C36) straight or branched chain alkyl or alkenyl alcohols or acids; short chain (i.e., C1-C6) alkyl or (C6-C12)aryl esters of (C4-C12)diacids or (C4-C12)diols optionally substituted in available positions by —OH; (C2-C18)alkyl or (C6-C12)aryl esters of glycerol, pentaerythritol, ethylene glycol, propylene glycol; (C12-C22)alkyl esters or (C12-C22)ethers of polypropylene glycol; (C12-C22)alkyl esters or (C12-C22)ethers of polypropylene glycol/polyethylene glycol copolymer; and long chain (i.e., C8-C36) alkyl and alkenyl esters of long (i.e., C8-C18) straight or branched chain alkyl or alkenyl alcohols or acids, long chain (i.e., C8-C36) alkyl and alkenyl amides of long straight or branched chain (i.e., C8-C36) alkyl or alkenyl amines or acids.

For certain embodiments, the emollient ester is selected from the group consisting of $(C_1-C_6)$alkyl and $(C_6-C_{12})$aryl esters of $(C_8-C_{36})$ straight or branched chain alkyl or alkenyl alcohols or acids; $(C_1-C_6)$alkyl and $(C_6-C_{12})$aryl diesters of $(C_2-C_{12})$diacids or $(C_4-C_{12})$diols, optionally substituted in at least one available position by —OH; $(C_1-C_6)$alkyl and $(C_6-C_{12})$aryl di- or tri-esters of citric acid, $(C_2-C_{18})$alkyl and $(C_6-C_{12})$aryl esters of glycerol, pentaerythritol, ethylene glycol, or propylene glycol; (C12-C22)alkyl esters and (C12-C22)ethers of polypropylene glycol; (C12-C22)alkyl esters and (C12-C22)ethers of polypropylene glycol/polyethylene glycol copolymer; long chain (i.e., $C_8$-C36) alkyl and alkenyl esters of long (i.e., C8-C18) straight or branched chain alkyl or alkenyl alcohols or acids, and long chain (i.e., C8-C36) alkyl and alkenyl amides of long straight or branched chain (i.e., C8-C36) alkyl or alkenyl amines or acids.

For certain embodiments, the emollient ester is selected from the group consisting of (C1-C6)alkyl and (C6-C12)aryl esters of (C8-C36) straight or branched chain alkyl or alkenyl alcohols or acids; (C1-C6)alkyl and (C6-C12)aryl diesters of (C2-C12) diacids or (C4-C12)diols, optionally substituted in at least one available position by —OH; and (C1-C6)alkyl and (C6-C12)aryl di- or tri-esters of citric acid.

Preferably, the emollient ester is present in the composition in an amount of at least 0.1 wt-%, more preferably at least 1 wt-%, and most preferably at least 2 wt-%. In preferred embodiments, the emollient ester is present in amounts of no more than 10.0 wt-%, more preferably no more than 6 wt-%. Higher levels can be used depending on the ratio of cationic antimicrobial agent to total nonvolatile components as discussed above.

Cationic Antimicrobial Agent

The cationic antimicrobial agent is that component of the composition that provides at least part of the antimicrobial activity. That is, the cationic antimicrobial agent has at least some antimicrobial activity for at least one microorganism. It is generally considered the main active component of the compositions described herein. The cationic antimicrobial agent includes an effective amount of one or more antimicrobial agents selected from the group consisting of biguanides and bisbiguanides such as chlorhexidine and its various salts including but not limited to the digluconate, diacetate, dimethosulfate, and dilactate salts, as well as combinations thereof; polymeric quaternary ammonium compounds such as polyhexamethylenebiguanide; small molecule quaternary ammonium compounds such as benzalkonium halides, benzethonium halides, alkyl substituted benzethonium halides, cetyl pyridinium halides; and compatible combinations thereof. It is particularly important, however, with cationic antimicrobial agents in a salt form to use a counter ion that ensures solubility in aqueous fluid above the minimum inhibitory concentration (MIC) of the treatment organism. If the solubility limit is less than the MIC, treatment may be ineffective.

For certain embodiments of the antimicrobial composition, the cationic antimicrobial agent is selected from the group consisting of chlorhexidine, chlorhexidine digluconate, chlorhexidine diacetate, chlorhexidine dimethosulfate, chlorhexidine dilactate salts, polyhexamethylenebiguanide, benzalkonium halides, octenidine, and combinations thereof.

For certain embodiments of the antimicrobial composition, the cationic antimicrobial agent is selected from the group consisting of chlorhexidine, chlorhexidine digluconate, chlorhexidine diacetate, chlorhexidine dimethosulfate, chlorhexidine dilactate salts, polyhexamethylenebiguanide, benzalkonium halides, and combinations thereof.

The cationic component is at least 10 wt-%, more preferably 15 wt-%, based on the total weight of the nonvolatile components in the composition. The cationic antimicrobial agent is preferably no more than 70 wt-%, and more preferably no more than 50 wt-%, based on the total weight of nonvolatile components in the composition.

Based on the total weight of the antimicrobial composition, cationic antimicrobial agents are typically used at levels of at least 0.05% by weight, preferably at least 0.1% by weight and most preferably at least 0.25% by weight and most preferably at least 0.5% by weight. Compounds of this class are preferably used at levels less than about 8%, more preferably less than about 6%, and most preferably less than about 4% by weight of the composition.

The classes of cationic antimicrobial agent suitable in the present invention are discussed further below.

Biguanides

This class of antimicrobials is represented by the formula:

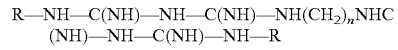
R—NH—C(NH)—NH—C(NH)—NH(CH$_2$)$_n$NHC
(NH)—NH—C(NH)—NH—R

Where n=3-10, preferably 4-8, and most preferably 6; and R=$C_4$-$C_{18}$ branched or straight chain alkyl optionally substituted in available positions by halogen or $C_6$-$C_{12}$ aryl or alkaryl optionally substituted in available positions by halogen.

The preferred compound of this class is chlorhexidine. This may be present as the free base but is preferably present as a disalt of acetate, gluconate, lactate, methosulfate (CH$_3$OSO$_3^-$), or a halide or combinations thereof. The most preferred compound is chlorhexidine digluconate (CHG).

Other anions may be useful. Many salts of chlorhexidine have high solubility (>1 g/100 mL) in alcohol/water systems and are therefore useful in compositions of this invention.

The antimicrobials of this class are typically used in formulations that include water and are protected from light. This is believed to reduce the degradation of the compound. When used in compositions comprising less than about 20% by weight water, antimicrobial agents of this class may also include a hydrophilic solvent that solubilizes the antimicrobial agent. Such solvents are miscible in alcohols and/or hydroalcoholic mixtures. Examples of suitable solvents for chlorhexidine gluconate include glycols (compounds having at least two hydroxyl groups per molecule) such as PEGs having a molecular weight below 2000 and preferably less than 1000 and most preferably less than about 800 daltons; glycerin and polyglycerols, propylene glycol, dipropylene glycol, tripropylene glycol, polypropylene glycol, ethylene oxide/propylene oxide random or block copolymers, trimethylolpropane, pentraerithiritol, sorbitol, panetothenol, glucuronolactone, gluconic acid, and the like as well as other polar solvents such as N-methylpyrrolidone, propylene carbonate, butyrolactone and the like. When used, the solubilizing solvent should be present in sufficiently low amounts to minimize sensitivity to water. Preferably, the solubilizing solvent is present in amounts less than 1 wt % relative to the weight of the total antimicrobial composition.

Care must also be taken when formulating chlorhexidine as well as other cationic antimicrobial compounds to avoid inactivation by sequestering it in micelles which may be formed by incorporation of surfactants and/or emulsifiers. Preferred compositions of this invention are essentially free of surfactants and/or emulsifiers.

Bis(biguanide)s such as chlorhexidine are very basic and capable of forming multiple ionic bonds with anionic materials. For this reason, biguanide-containing compositions are preferably free of anionic compounds that can result in precipitation of the antimicrobial. Anionic surfactants useful, for example, as wetting agents, may also need to be avoided. Halide salts may need to be avoided. For example, chlorhexidine digluconate (CHG) will precipitate rapidly in the presence of halide salts above a concentration of about 0.1M. Therefore, if a system includes CHG or other antimicrobial of this class, and needs to comprise salts for stability or other purposes, preferably gluconate salts such as triethanolamine gluconate or sodium gluconate, are used.

Polymeric Quaternary Amine Compounds

Antimicrobial polymers comprising quaternary amine groups may also be used as the cationic antimicrobial agent in the compositions described herein. These are typically polymers having quaternary amine groups with at least one alkyl or aralkyl chain of at least 6 carbon atoms and preferably as least 8 carbon atoms. The polymers may be linear, branched, hyperbranched or dendrimers. Preferred antimicrobial polymeric quaternary amine polymers include those described in U.S. Pat. Nos. 6,440,405; 5,408,022; and 5,084,096; PCT Publication No. WO/02102244; and *Disinfection, Sterilization and Preservation*, S. Block, 4$^{th}$ ed., 1991, Chapter 13, Lea & Febiger.

A particularly preferred class of polymeric quaternary ammonium antimicrobial compounds are polybiguanides. Compounds of this class are represented by the formula:

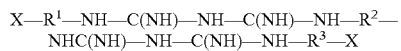

Where $R^1$, $R^2$, and $R^3$ are bridging groups such as polymethylene groups preferably having 2 to 10 methylene groups, more preferably 4 to 8 methylene groups and most preferably 6 methylene groups. The methylene groups can be optionally substituted in available positions with halogen, hydroxyl, or phenyl groups. X is a terminal group and is typically an amine, amine salt, or a dicyandiamide group. The preferred compound of this class is polyhexamethylene biguanide (PHMB) commercially available as Cosmocil CQ from Aveci, Wilmington, Del.

Poly(biguanide) antimicrobials such as PHMB are very basic and are capable of forming multiple ionic bonds with anionic materials. For this reason, biguanide-containing compositions are preferably free of anionic compounds that can result in precipitation and/or inactivation of the antimicrobial. Anionic surfactants useful, for example, as wetting agents, may also need to be avoided. Halide salts also may need to be avoided.

Small Molecule Quaternary Ammonium Compounds

This class of compounds typically comprise one or more quaternary ammonium groups wherein attached to the quaternary ammonium group is at least one $C_6$-$C_{18}$ linear or branched alkyl or aralkyl chain. Suitable compounds include those disclosed in *Disinfection, Sterilization and Preservation*, S. Block, 4$^{th}$ ed., 1991, Chapter 13, Lea & Febiger. Particularly preferred compounds of this class have one or two $C_8$-$C_{18}$ alkyl or aralkyl chains and may be represented by the following formula:

Where $R^1$ and $R^2$ are $C_1$-$C_{18}$ linear or branched alkyl, alkaryl, or aralkyl chains that may be substituted in available positions by N, O, or S provided at least one $R^1$ or $R^2$ is a $C_8$-$C_{18}$ linear or branched alkyl, alkaryl, or aralkyl chains that may be substituted in available positions by N, O, or S. $R^3$ and $R^4$ are $C_1$-$C_6$ alkyl, phenyl, benzyl, or $C_8$-$C_{12}$ alkaryl groups. $R^3$ and $R^4$ may also form a ring such as a pyridine ring with the nitrogen of the quaternary ammonium group. X is an anion, preferably a halide, and most preferably $C_1$- or Br—. Other anions may include methosulfate, ethosulfate, phosphates and the like. Preferred compounds of this class include mnoalyltrimethylammonium salts, monalkyldimethylbenzyl ammonium salts, dialkyldimethyl ammonium salts, benzethonium chloride, and octenidine.

Examples of preferred quaternary ammonium antiseptics include benzalkonium halides having an alkyl chain length of $C_8$-$C_{18}$, more preferably $C_{12}$-$C_{16}$, and most preferably a mixture of chain lengths. For example, a typical benzalkonium chloride sample may be comprise of 40% $C_{12}$ alkyl chains, 50% $C_{14}$ alkyl chains, and 10% $C_{16}$ alkyl chains. These are commercially available from numerous sources including Lonza (Barquat MB-50); Benzalkonium halides substituted with alkyl groups on the phenyl ring. A commercially available example is Barquat 4250 available from Lonza; dimethyldialkylammonium halides where the alkyl groups have chain lengths of $C_8$-$C_{18}$. A mixture of chain lengths such as mixture of dioctyl, dilauryl, and dioctadecyl may be particularly useful. Exemplary compounds are commercially available from Lonza as Bardac 2050, 205M and 2250 from Lonza; Cetylpyridinium halides such as cetylpyridinium chloride available from Merrell labs as Cepacol Chloride; Benzethonium halides and alkyl substituted benzethonium halides such as Hyamine 1622 and Hyamine 10× available from Rohm and Haas; octenidine and the like.

Optional Fatty Component

The antimicrobial composition can also optionally include a fatty component as a cidatrope that provides improved antimicrobial efficacy to the antimicrobial composition. The fatty component preferably comprises at least 12 carbon atoms, and most preferably at least 14 carbon atoms. The fatty component preferably comprises no more than 21 carbon atoms, and preferably no more than 18 carbon atoms.

Fatty components suitable for use as a cidatrope in the antimicrobial compositions include a $C_{12}$-$C_{21}$ fatty alcohol, a $C_{12}$-$C_{21}$ fatty ester containing one or more free hydroxyl groups, a $C_u$-$C_{21}$ fatty ether containing one or more free hydroxyl groups, a $C_{12}$-$C_{21}$ fatty amide containing one or more free hydroxyl groups, and combinations thereof. The fatty components are preferably linear alkyl chains, but branched alkyl chains may also be used.

The fatty component of the composition, along with the hydrophobic polymer and emollient ester, can also contribute to the improved adhesion of medical adhesive articles to the skin, particularly in the presence of moisture or fluids. The fatty component is also preferably waxy to improve the overall cosmetic skin feel of the composition as well.

The fatty components are preferably not ethoxylated. Ethoxylation affects the moisture sensitivity of the resultant antimicrobial composition, with a resulting decrease in adhesion performance. If any one of the components is ethoxylated, it is preferably no more than one or two moles of ethylene oxide.

When used, the fatty component is present in the composition in an amount of at least 0.5 wt-%, more preferably at least 1 wt-%, even more preferably at least 2 wt-%, and most preferably at least 3 wt-% based on the total weight of the antimicrobial composition. In certain embodiments, the fatty component is present in amounts of no more than 6 wt-%, and more preferably no more than 5 wt-%. Higher levels can be used depending on the ratio of cationic antimicrobial agent to total nonvolatile components in the antimicrobial composition as discussed above.

Fatty Alcohols

The class of fatty alcohols suitable for use in the compositions described herein include a straight or branched chain alkyl, alkenyl or aralkyl alcohol comprising at least 12 carbon atoms, and most preferably at least 14 carbon atoms. The fatty alcohol comprises at most 21 carbon atoms, and preferably at most 18 carbon atoms. The fatty alcohols are preferably primary fatty alcohols, although secondary or tertiary alcohols are also effective. Examples of suitable $C_{12}$-$C_{21}$ fatty alcohols include but are not limited to lauryl alcohol, myristyl alcohol, cetyl alcohol, isostearyl alcohol, isocetyl alcohol, octyl dodecanol, 2-hexyl decanol, and 2-hexyl dodecanol. Preferably, the $C_{12}$-$C_{21}$ fatty alcohol is a wax at ambient conditions.

Particularly preferred $C_{12}$-$C_{21}$ fatty alcohols are myristyl alcohol and cetyl alcohol. Cetyl alcohol or 1-hexadecanol provides enhanced and preferably synergistic bactericidal activity with cationic antimicrobial agents, and acceptable cosmetic feel when applied topically. Cetyl alcohol is safe, non-irritating, and is widely used in pharmaceutical and drug creams. It also provides water resistance to the formula after it is applied to the skin, thereby contributing to improved skin adhesion of medical adhesive articles to the composition. In amounts above 2 wt-% based on the total weight of the antimicrobial composition, the $C_{12}$-$C_{21}$ fatty alcohols contribute to improved skin adhesion under wet conditions.

Fatty Ester

The class of fatty esters suitable for use in the compositions are $C_{12}$-$C_{21}$ fatty acid esters comprising a $C_{12}$-$C_{18}$ branched or straight chain alkyl group, at least one ester linkage, and at least one free hydroxyl group. Preferably, the fatty acid esters are highly pure, i.e. fatty acid monoesters, fatty acid diesters.

A subset of this class suitable for use in the compositions described herein includes a ($C_{12}$-$C_{18}$) saturated or unsaturated fatty acid ester of a polyhydric alcohol. Preferably, the fatty acid ester is a ($C_{12}$-$C_{18}$) saturated fatty acid ester of a polyhydric alcohol. A fatty acid ester of a polyhydric alcohol is preferably of the formula $(R^1-C(O)-O)_n-R^2$, wherein $R^1$ is the residue of a ($C_{12}$-$C_{16}$) saturated fatty acid (preferably, a ($C_{12}$-$C_{16}$) saturated fatty acid), or a ($C_{12}$-$C_{18}$) unsaturated (preferably, a $C_{12}$-$C_{16}$) unsaturated, including polyunsaturated) fatty acid, $R^2$ is the residue of a polyhydric alcohol (typically and preferably, glycerin, and propylene glycol, although a wide variety of others can be used including butylene glycols, hexylene glycols, and diols), and n=1 or 2. The $R^2$ group includes at least one free hydroxyl group (preferably, residues of glycerin or propylene glycol). Preferred fatty acid esters of polyhydric alcohols are esters derived from $C_{12}$, $C_{14}$, and $C_{16}$ saturated fatty acids. For embodiments in which the polyhydric alcohol is glycerin or propylene glycol, n=1. Diesters of glycerin (n=2) also may be suitable.

Exemplary fatty acid monoesters include, but are not limited to, glycerol monoesters of lauric (monolaurin), myristic, and palmitic acid, and propylene glycol monoesters of lauric, myristic, and palmitic acid. Other fatty acid monoesters include glycerin and propylene glycol monoesters of oleic (18:1), linoleic (18:2), linolenic (18:3), and arachonic (20:4) unsaturated (including polyunsaturated) fatty acids. As is generally know, 18:1, for example, means the compound has 18 carbon atoms and 1 carbon-carbon double bond. Preferred unsaturated chains have at least one unsaturated group in the cis isomer form.

Another subset of fatty acid esters suitable for use as the fatty component include ($C_{12}$-$C_{21}$) fatty alcohol ester of a ($C_2$-$C_8$) hydroxycarboxylic acid (also often referred to as a ($C_2$-$C_8$) hydroxycarboxylic acid ester of a ($C_{12}$-$C_{18}$) fatty alcohol), a ($C_{12}$-$C_{22}$) mono- or poly-unsaturated fatty alcohol ester of a ($C_2$-$C_8$) hydroxycarboxylic acid (also often referred to as a ($C_2$-$C_8$) hydroxycarboxylic acid ester of a ($C_{12\text{-}18}$) mono- or poly-unsaturated fatty alcohol). The hydroxycarboxylic acid moiety can include aliphatic and/or aromatic groups. For example, fatty alcohol esters of salicylic acid are possible.

The hydroxyacids typically have one hydroxyl group and one carboxylic acid group. They are preferably selected from alpha- and beta-hydroxyacids including lactic acid, mandelic acid, glycolic acid, salicylic acid, and hydroxybutanoic acid. The fatty alcohols are most preferably straight or branched alkyl alcohols having 12 to 18 carbon atoms, and most preferably 12 to 16 carbon atoms or a ($C_{12}$-$C_{20}$) unsaturated fatty alcohol (preferably, a $C_{12}$-$C_{18}$) unsaturated, including polyunsaturated, fatty alcohol). Examples of fatty alcohols include lauryl, myristyl, cetyl, and their derivatives.

Exemplary fatty alcohol monoesters of hydroxycarboxylic acids include, but are not limited to; $C_{12}$-$C_{15}$ alkyl lactates, lauryl lactate, myristyl lactate, cetyl lactate, and isostearyl lacatate.

Fatty Ethers

The class of fatty ethers suitable for use in the compositions are $C_{12}$-$C_{21}$ fatty acid ethers comprising a $C_{12}$-$C_{18}$ branched or straight chain alkyl group, at least one ether linkage, and at least one free hydroxyl group. A subset of fatty ethers suitable for use in the antimicrobial compositions include a ($C_{12}$-$C_{18}$) saturated or unsaturated fatty ether of a polyhydric alcohol. Preferably, the fatty ether is a ($C_{12}$-$C_{16}$) saturated fatty ether of a polyhydric alcohol.

A fatty ether of a polyhydric alcohol is preferably of the formula $(R^3-O)_n-R^4$, wherein $R^3$ is a ($C_{12}$-$C_{18}$) saturated aliphatic group (preferably, a ($C_{12}$-$C_{16}$) saturated aliphatic group), or a ($C_{12}$-$C_{18}$) unsaturated (preferably, ($C_{12}$-$C_{16}$) unsaturated, including polyunsaturated) aliphatic group, $R^4$ is the residue of glycerin, butylene glycol, or propylene glycol, and n=1 or 2. For glycerin and propylene glycol n=1. Preferred fatty ethers are monoethers of ($C_{12}$-$C_{18}$) alkyl groups (more preferably, ($C_{12}$-$C_{16}$ alkyl groups).

Exemplary fatty monoethers include, but are not limited to, lauryl glyceryl ether and lauryl propylene glycol ether. Other fatty monoethers include glycerin and propylene glycol monoethers of oleyl (18:1), linoleyl (18:2), and linolenyl (18:3) unsaturated and polyunsaturated fatty alcohols. In certain preferred embodiments, the fatty monoethers that are suitable for use in the present composition include lauryl glyceryl ether, myristyl glycerylether, lauryl propylene glycol ether, cetyl propylene glycol ether, and combinations thereof. Unsaturated chains preferably have at least one unsaturated bond in the cis isomer form.

Additional Optional Ingredients

The compositions of the present invention may optionally include ingredients such as salts, humectants (in minimal amounts due to their hydrophilic nature and affect on moisture sensitivity), stabilizers, other antimicrobials, fragrances, therapeutic agents, propellants, dyes, solvents, other emollients, conditioning agents, and vitamins. Preferred solvents include acetone, dimethylisosorbide, and isooctane.

Optionally hydrophilic surfactants and other additives may be added to the antimicrobial composition as long as the dried composition forms a water resistant film as described above.

Preferably, the formulations are essentially free of surfactants. Most preferably, the compositions do not contain surfactants in any measurable quantity. For certain embodiments, surfactants of which the formulations are essentially free are hydrophilic surfactants. Hydrophilic surfactants increase the water sensitivity of the formulations when applied on the skin and decrease adhesive performance. If present, the surfactants preferably have an HLB (hydrophilic to lipophilic balance) less than 8, more preferably less than 6, and even more preferably less than 4. Examples of surfactants include glycerol palmitate, poloxamers, polyglycerol esters, PEG-esters, and sorbitan esters.

For certain embodiments, the antimicrobial compositions are essentially free of ionic surfactants with the exception of those that have antimicrobial activity and would be considered an antimicrobial component.

Preferably, the compositions are essentially free of hydrophilic polymers, and water-soluble or water swellable polymers.

It should be noted that certain fatty components of the fatty acid ester class as well as the emollient esters are amphiphiles and may be surface active. For example, certain alkyl monoglycerides described herein are surface active. For certain embodiments of the invention, the emollient ester component, and the fatty component when used, are considered distinct from a "surfactant" component.

Methods of Formulation

When formulating compositions described herein, it is desirable to have the emollient ester as a liquid. By using a combination of the hydrophobic polymer and emollient ester, the resulting compositions have more elegant skin feel and dry quickly. For example, most emollient esters present without the hydrophobic polymer in the composition above concentrations of 0.5% (w/w) would be slow to dry and leave an undesirable oily film on the skin when applied topically. By incorporating a hydrophobic polymer, and optionally a fatty component, into the composition, the composition dries faster, loses its oily feel, and becomes cosmetically acceptable.

Furthermore, by using a combination of the hydrophobic polymer and the emollient ester, the amount of each component that can be used in the formula is much greater than if either were used alone. Using greater amounts of the hydrophobic polymer or emollient ester is highly desirable, because increasing the concentration of either component increases the water insensitivity of the dried film and the antimicrobial efficacy of the composition. By using both a hydrophobic polymer and an emollient ester, the compositions show both desirable skin feel and improved antimicrobial efficacy.

Generally, the hydrophobic polymer/emollient ester ratio in compositions described herein is about 5:1 to 1:10. Preferably, the ratio is greater than 1:2, and most preferably about 1:1. Preferably, both the hydrophobic polymer and emollient ester are soluble in the lower alcohol/water solution and do not precipitate over time. Most preferably, the hydrophobic polymer is a solid at ambient temperature. Without being bound to a particular theory, it is believed that the emollient esters interact with the outer cellular membranes of bacteria in such a manner that synergistically enhances the activity of the cationic antimicrobial agent.

The compositions of this invention are especially useful for preoperative surgical, catheter, and i.v. antiseptic preps. They are also useful for preventing or reducing catheter related bloodstream infections. For these formulations, enhanced wet adhesion and enhanced antimicrobial efficacy are two advantages that are important. Preferred formulations according to the invention for these preps contain a significant amount of hydrophobic polymer, preferably greater than 2 wt %, most preferably greater than 2.5 wt %. Ideally, the hydrophobic polymer should be as hydrophobic as possible (yet maintain solubility or dispersibility in the hydroalcoholic solution) and solid, with a melting point or Tg greater than 25° C., in order to enhance the adhesion of dressings in wet conditions.

The compositions also contain an emollient ester, which preferably does not block skin pores and further provides enhanced antimicrobial efficacy. Preferred emollient esters according to the invention for catheter and i.v. preps include diisopropyl adipate, dibutyl adipate, and tributyl citrate at concentrations greater than 1 wt %, preferably greater than 1.5 wt %. The compositions also contain about 2% (w/w or w/v) chlorhexidine gluconate to meet Center for Disease Control (CDC) guidelines for preventing cathether-related blood stream infections. They would also comprise a majority amount of $C_2$-$C_5$ alcohol, preferably greater than 65 wt-%, so that the formulation will dry quickly after topical application. Catheter prep compositions will also preferably contain no humectants or other water soluble materials (including surfactants), which could undermine dressing adhesion under wet conditions. This is particularly important because small amounts of surfactants, especially fatty alcohol ethoxylates, can significantly undermine adhesion in the presence of moisture including sweat, saline, blood, and water. Small amounts of humectants such as glycols or glycerol may be used in some embodiments of the compositions, but most compositions are preferably free of humectants.

The compositions of this invention are also useful for hand antiseptics and surgical scrubs. For this application, adhesion of medical adhesive articles may be less significant but enhanced efficacy and superior skin feel are very important. For hand antiseptics, the compositions will preferably contain greater than 60 wt % lower alcohol and about 2-8 wt % of hydrophobic components comprising a hydrophobic polymer, emollient ester, and optionally a fatty component. Humectants may also be used as moisture sensitivity of the compositions is less critical in hand antiseptic applications. Most preferably, the compositions will contain greater than 70 wt % alcohol to provide an immediate and significant reduction of transient and normal flora of the hands. In addition, the compositions would comprise preferably 0.3 to 1.5 wt % of a nonvolatile antimicrobial cationic agent, and most preferably 0.4 to 1.0 wt %.

Because water sensitivity is less important in hand antiseptic applications, a large variety of hydrophobic polymers can be potentially used. Preferably, the compositions also contain a light feeling, liquid emollient ester such as tributyl citrate or diisopropyl adipate and a small amount of humectant. Using the combination of a solid hydrophobic polymer and liquid emollient ester results in superior skin feel compared to compositions containing only one of these components alone. Furthermore, the use of both components together allows for the use of higher concentrations of both the hydrophobic polymer and emollient ester. Furthermore, the use of higher concentrations of these components counteracts the drying effect and irritation of the skin caused by the lower alcohol in these compositions especially with repeated application. Lower alcohols (such as ethanol) by themselves are known to be drying especially at higher concentrations. Optionally, the formulations may contain other emollients such as higher molecular weight waxes and oils that do not enhance antimicrobial efficacy, but lower the transepidermal water loss (TEWL) of skin.

The compositions of this invention are also useful for preventing and treating skin infections. The compositions may be used to prevent surgical site infection by applying the compositions to the skin prior to surgery. When the compositions contain chlorhexidine gluconate, the skin may be preferably treated topically less than about 30 hours prior to surgery, and most preferably less than 10 hours prior to surgery. These compositions can be applied to reduce the transient and normal flora of the skin. Repeated applications may be used to provide even higher efficacy (log reduction of bacteria) on the skin. In a preferred embodiment, the formulations are used a preoperative surgical prep or skin antiseptic.

Likewise, the compositions of this invention can be used to prevent catheter related bloodstream infections. Specifically, the compositions are applied topically to the skin for 30-180 seconds and allowed to dry for 30-180 seconds or for a time period such that the alcohol evaporates. The remaining layer of nonvolatile components surprisingly provide enhanced antimicrobial activity that is persistent for long periods of time. After the composition is applied and visually dry, a catheter or intravenous line can be inserted and secured with a transparent dressing. The nonvolatile components remain under the dressing as a highly active, persistent bactericidal layer on the skin.

The compositions can be used in the treatment and/or prevention of afflictions that are caused, or aggravated by, microorganisms (e.g., Gram positive bacteria, Gram negative bacteria, fungi, protozoa, mycoplasma, yeast, viruses, and even lipid-enveloped viruses) on skin and/or mucous membranes, such as those in the nose (anterior nares, nasopharangyl cavity, nasal cavities, etc.), outer ear, and mouth, rectum, vagina, or other similar tissues. Particularly relevant organisms that cause or aggravate such afflications include *Staphylococcus* spp., *Streptococcus* spp., *Pseudomonas* spp., *Enterococcus* spp., and *Esherichia* spp., bacteria, as well as herpes virus, *Aspergillus* spp., *Fusarium* spp. *Candida* spp. as well as combinations thereof. Particularly virulent organisms include *Staphylococcus aureus* (including resistant strains such as Methicillin Resistant *Staphylococcus Aureus* (MRSA), *Staphylococcus epidermidis*, *Streptococcus pneumoniae*, *Enterococcus faecalis*, Vancomycin Resistant *Enterococcus* (VRE), *Pseudomonas auerginosa*, *Escherichia coli*, *Aspergillus niger*, *Aspergillus fumigatus*, *Aspergillus clavatus*, *Fusarium solani*, *Fusarium oxysporum*, *Fusarium chlamydosporum*, *Candida albicans*, *Candida glabrata*, *Candida krusei*, and combinations thereof.

Compositions of the present invention can be used for the prevention and/or treatment of one or more microorganism-caused infections or other afflictions. In particular, compositions of the present invention can be used for preventing and/or treating one or more of the following—skin lesions, conditions of the skin such as impetigo, eczema, diaper rash in infants as well as incontinent adults, inflammation around ostomy devices, shingles, and bacterial infections in open wounds (e.g., cuts, scrapes, burns, lacerations, chronic wounds); necrotizing faciitis; infections of the outer ear; vaginal yeast infections; bacterial rhinitis; ocular infections; cold sores; genital herpes; colonization by *Staphylococcus aureus*; tinea pedis (i.e., athlete's foot); tinea curis (i.e., jock itch); tinea corporis (i.e., ringworm); candidiasis; strep throat, strep pharyngitis, and other Group A Streptococci infections; rosacea (often called adult acne); psoriasis; and burns. In sum, compositions of the present invention can be used for preventing and/or treating a wide variety of topical afflictions caused by microbial infection (e.g., yeast, viral, bacterial infections).

The compositions are particularly useful because lower alcohols, and some of the fatty components if used, are known skin penetration enhancers and can deliver the nonvolatile components to deeper layers of the skin. Furthermore, the lower alcohol can disinfect the skin as well providing an immediate log reduction of microorganisms on skin.

Methods of Application

The compositions can be applied using a variety of techniques including but not limited to: foamed applicators, cotton swabs, saturated swab sticks, saturated wipes, aerosols, sprays, brushes, and dips. Preferably, the compositions are contacted with the skin or inanimate object for 15 to 180 seconds and then allowed to dry. They may be used as a paint or as a surgical scrub. Because of the unique characteristics of the inventive compositions, the compositions are particularly useful for infection prevention products such as a preoperative antiseptic surgical preparations and antiseptic skin preparations used prior to catheterization. These compositions are particularly useful when used in conjunction with medical adhesives, tapes, surgical drapes, and transparent dressing under wet or suboptimal conditions.

Since many of the compositions of the present invention contain antimicrobials, it is important that they be dispensed in an efficacious and precise amount. The compositions of the present invention can be dispensed in a discreet, substantially uniform amount using the dispensers disclosed in U.S. Pat. No. 5,897,031, and U.S. Pat. No. 5,799,841.

METHODS OF PREPARATION

The compositions of the present invention may be prepared by a variety of techniques. The processing variables including amount and intensity of high shear mixing, rate of cooling, and order of addition are easily determined by one skilled in the art.

TEST METHODS

Skin Adhesion Test Protocol

Volunteer human test subjects were used for the Skin Adhesion Testing. The subjects' backs were washed with a diluted Ivory soap, rinsed and dried well. The test compositions were applied to their backs by simply painting the site with gauze saturated with the test composition using moderate pressure three times in a continuous circular motion. After allowing the test composition to dry, 1 inch×3 inch (2.54 cm×7.6 cm) strips of 3M IOBAN 2 Antimicrobial Incise Drape were very gently applied over the dry composition. Within 5 minutes the samples were rolled with a 4.5-lb (2.1-kilogram (kg)), 2-inch (5.1 cm) roller to ensure uniform application pressure and to simulate conditions in surgery. After the drape was applied, there was a 5 minute waiting period. A piece of gauze (large enough to cover the sample) soaked with saline was applied, followed by another 5 minute waiting period. An additional 3 mL of saline was added to the gauze followed by another 5 minute waiting period. The gauze was removed from the samples. The incise drape strip was removed using a force-measuring instrument at a peel angle of 90 degrees to the skin and at a peel rate of 12 inches (30.5 cm) per minute. The average peel force was calculated based on twenty tests across ten subjects (two per subject). The average peel force required to remove the sample was recorded.

Direct Inoculation Filter Assay

This is an in vitro assay using filter paper to compare the residual efficacy of different surgical skin prep formulations.

Phosphate Buffered Water solution (PBW) was made by making a 0.25M stock solution by putting 34 grams $KH_2PO_4$ into 500 mL of DI water, adjusting the pH to 7.2 with 10N NaOH, and adding enough DI water to make 1 liter. The solution was filtered, sterilized, dispensed into a 1 liter sterile bottle, and stored under refrigeration. Butterfield's PBW was made by adding 1.25 mL of the stock solution to 900 mL of DI water and adding neutralizers, stirring, heating to dissolve the components, and diluting to 1 liter with DI water. The solution was mixed well, dispensed into two 500-mL bottles. The bottles containing the solution were autoclaved for 25 minutes at 121 degree C. The contents were carefully swirled after removing the bottles from the autoclave.

A Standard Sampling Solution (SSS) was prepared which contained: 0.4 grams $KH_2PO_4$, 10.1 grams $Na_2HPO_4$, 1.0 gram TRITON X-100 surfactant, 3.0 grams lecithin, 30.0 grams TWEEN 80, and deionized water to bring the total volume to 1 liter.

Additional solutions and materials included: 24 hour growth plate of E. faecalis; ATCC #10741; Tryptic Soy Agar (TSA); 0.5 McFarland Equivalence Turbidity standard, available from Remel of Lenexa, Kans.; sterile disposable dilution tubes, available from Becton Dickenson & Co. Franklin Lakes N.J.; Whatman No. 54 filter paper, cut into 15 mm diameter circles, Whatman International, Ltd., Maidstone, England; sterile round microscope cover slips, available from VWR Scientific, Inc. of Media Pa.; microscope slides, available from VWR; sterile forecepts; 70% Isopropyl Alcohol (IPA); sterile disposable petri plates, available from VWR; sterile 50 mL centrifuge tubes available from Becton Dickenson & Co. Franklin Lakes N.J.; digital timers; pipets and pipettors of appropriate volumes.

A stock suspension of E. faecalis was prepared by adding colonies to test tube containing PBW. Using the 0.5 McFarland Equivalence Turbidity Standard, the suspension was brought to approximately $1.5 \times 10^8$. Serial dilutions were performed to achieve $10^{-6}$ and plate in duplicate $10^{-6}$ and $10^{-7}$. For each Example, Comparative preparation or Control (70% IPA), a microscope slide was wiped with 70% IPA and placed in the bottom of a petri dish. Using sterile forecepts, two sterile 18 mm round cover slips were placed side-by-side on the slide, and then a 15 mm round cut Whatman filter disc was placed on each of the round cover slips.

Onto each filter disc was pipetted 25 µL of each Example, Comparative preparation or Control. These discs were allowed to dry for 10 minutes. After 10 minutes of dry time, 25 µL of stock suspension of E. faecalis was pipetted onto each filter. The inoculum was left on the filters for 5 minutes. After the 5 minute inoculum exposure time, sterile forecepts were used to place each cover slip and filter disc into a 50 mL centrifuge tube containing 20 mL SSS solution. Each Example, Comparative preparation or Control was vortexed in the centrifuge tubes for 2 minutes. Next, 100 µL of each Example or control was diluted in a dilution tube containing 9.9 mL PBW, to yield a $10^{-2}$ dilution. Serial dilutions were repeated to achieve a $10^{-4}$ dilution. Dilutions were plated in duplicate with TSA using pour plate methods and incubated for 48 hours at 35° C. After 48 hours, colonies were counted and recorded.

The CFU/mL was determined by multiplying CFU count by dilution rate. The CFU/sample was calculated by multiplying the CFU/mL by 20, the amount of the SSS dilution. The $\log_{10}$ of the CFU/sample was calculated. This was the Log Recovery for each sample. The log recovery values were averaged for the replicates of each sample (Example) and control. The log recovery value of each Example was subtracted from the log recovery of the control. The result is the log reduction for that Example preparation. The log recovery of control was verified as statistically equal to calculated inoculum amount, based on enumeration of stock suspension. Unless stated otherwise, log reduction values reported below are the average of duplicate preparations.

Skin Panel Evaluation

The purpose of this study was to assess the antimicrobial efficacy of selected Example formulations, which represent embodiments of the invention and an alcohol/CHG comparative example. The reduction of normal skin flora on backs at was measured 10 minutes post prep.

Two weeks (14 days) prior to the Study Day, human test subjects followed a washout procedure by refraining from using antimicrobial soaps & shampoos, lotions (on the back) and topical and systemic antibiotics; refraining from using chemically treated hot tubs, whirlpools, swimming pools and tanning beds; refraining from adhesive back panel evaluations and/or antimicrobial or antiseptic back panel evaluations; refraining from showering or tub bathing the back (the subject may sponge bathe) 24 hours prior to the study. If clipping was required the subject returned to the panel facility a minimum of 48 hours prior to Study Day.

On The Study Day the "Study Day Questionnaire" was completed which determined if the subject had been compliant with the washout procedures and was still eligible for participation. A randomization scheme for each back determined location of baseline sampling and treatment (prepped) test sites. Baseline sampling of skin flora was done using the Williamson-Kligman cup scrub technique. Each prep formulation was applied to the appropriate test site with a sponge using a back and forth motion for 30 seconds covering an approximate 2 inch×2 inch area. Prepped sites were allowed to dry and post treatment skin samples were taken at 10 minutes (±1 min) using the Williamson-Kligman cup scrub technique. Timing for sample collection began after application.

The neutralization subject washout was for 7 days and was not required to refrain from showering or tub bathing 24 hours before the test day. The samples were collected using the Williamson-Kligman cup scrub technique.

Willimson-Kligman Cup Scrub Technique

A sterile scrub cup was placed on the desired skin site and held firmly to the skin. 2.5 mL of sampling solution was pipetted into the cup and the area was scrubbed with moderate pressure for 1 minute using a sterile Teflon policeman. The sampling solution was removed and placed in a sterile test tube. An additional 2.5 mL of fresh sampling solution was pipetted into the cup. The scrub was repeated and this solution was pooled with the first. Bacteria in the sample were enumerated using the pour plate technique following serial dilutions in phosphate buffered water. Plates were incubated at 35° C.±2° C. for 72±4 hours. Colony Forming Units (CFUs) were counted and bacteria enumerated using standard methods.

The sampling solution for skin scrubbing consisted of phosphate buffer (0.04% $KH_2PO_4$, 1.01% $Na_2HPO_4$) containing 0.1% Triton X-100, 3.0% Tween 80, and 0.3% Lecithin, adjusted to pH 7.9±0.1. The adequacy and efficacy of the neutralizers in these solutions was validated by an in vitro method prior to study conduct.

EXAMPLES

The following non-limiting Examples are provided to illustrate features of the invention but are not intended to limit the scope of the invention. All percent amounts are percent weight/weight (% wt/wt) unless otherwise noted.

TABLE 1

| | Components | | |
|---|---|---|---|
| Trade/Abbrev. Name | Description | Supplier/Manf. | Manf. Location |
| Acetone | Acetone | EMD Chemicals, Inc. | Gibbstown, NJ |
| ATBC | Acetyl Tributyl Citrate | Morflex Inc. | Greensboro, NC |
| ATEC | Acetyl Triethyl Citrate, NF | Morflex Inc. | Greensboro, NC |
| CHG | 20% Chlorhexidine Digluconate solution | Xttrium Laboratories | Chicago, IL |
| DBS | Dibutyl sebacate | Morflex Inc. | Greensboro, NC |
| DIPA | Diisopropyl adipate; (CERAPHYL 230) | ISP; International Specialty Products | Wayne, NJ |
| DIPS | Diisopropyl sebacate | JEEN International Corp. | Fairfield, NJ |
| Disodium phosphate | $Na_2HPO_4$, ACS grade | EMD Chemicals, Inc. | Gibbstown, NJ |
| EtOH | Ethyl alcohol; ethanol, USP 200 proof | Spectrum Chemicals and Lab Products | Gardena, CA |
| Ethocel 100 | Ethylcellulose polymer | Dow Chemical Co. | Midland, MI |
| E. faecalis | Enterococcus faecalis (ATCC #10741) | ATCC | Manassas, VA |
| FD&C Blue No. 1 | FD&C Blue No. 1 food safe dye | Sensient Technologies Corporation | Milwaukee, WI |
| Glycerin | Glycerin USP | Procter & Gamble Chemicals | Cincinnati, OH |
| Glycerol | Superol Glycerine USP | Procter & Gamble Chemicals | Cincinnati, OH |
| IPA | Isopropyl alcohol | EMD Chemicals, Inc. | Gibbstown, NJ |
| Lecithin | Refined Lecithin | AlfaAesar | Ward Hill, MA |
| Myristyl OH | Myristyl Alcohol | M. Michel and Company, Inc. | New York, NY |
| Permethyl 97A | Isooctane | Chesham Speciality Ingredients Ltd | Harrow, UK |
| Permethyl 99A | Isododecane | Chesham Speciality Ingredients Ltd | Harrow, UK |
| PVP | Polyvinyl pyrrolidone K90 100% powder: 1,300,000 weight average molecular weight (Mw) in Daltons | ISP (International Specialty Products) | Wayne, NJ |
| TBC | Tributyl citrate | Morflex Inc. | Greensboro, NC |
| TEC | Triethyl citrate, NF | Morflex Inc. | Greensboro, NC |
| Triton X-100 | $C_{14}H_{22}O(C_2H_4O)_n$ is a nonionic surfactant; Molecular Biology Certified | Shelton Scientific, Inc. | Shelton, CT |
| TSA | Tryptic soy agar; Soybean Casein Digest Agar | Becton Dickinson & Co. | Sparks, MD |
| Tween 80 | Polyoxyethylene (20) sorbitan monoleate | J T Baker (Mallinckrodt Baker, Inc.) | Philliopsburg, NJ |

Examples 1-6

CHG Control Examples and Comparative Examples C1-C3

The Examples shown in Tables 2 and 3 were prepared in 60 gram quantities in the following manner. To a first vessel, the designated amounts of the following ingredients were added: ethyl cellulose, DIPS, DIPA, ethanol and glycerol. This first vessel was heated to 50° C. To a second vessel, the designated amounts of CHG and water were mixed. The second vessel was swirled to mix the CHG mixture, while the contents of the first vessel were added to the second vessel. The formulations were further homogenized for 30 seconds at high speed using a Silverson homogenizer equipped with a small square hole emulsifier head. The examples were then allowed to cool to room temperature on a lab bench. The amounts of the components in Tables 2 and 3 are in grams unless otherwise noted. The total weight of each prepared Example was 60 grams. These formulations were tested according to the Direct Inoculation Filter Assay described above. Additionally, each formulation was evaluated for skin feel by placing about 0.5 g of the formulation on a forearm and allowing the formulation to dry for about 90 seconds followed by evaluation of the treated skin with a clean finger. The results are also shown in Tables 2 and 3, below.

TABLE 2

| Components | Ex. 1 | Ex. 2 | Ex. 3 | Ex. 4 | Control 0.5% CHG | Control 1% CHG | Control 2% CHG | Control 4% CHG |
|---|---|---|---|---|---|---|---|---|
| Ethocel 100 | 0.6 | 0.6 | 0.6 | 0.6 | — | — | — | — |
| DIPS | 0.6 | 1.2 | 0.3 | 0.9 | — | — | — | — |
| Glycerol | 0.12 | 0.12 | 0.12 | 0.12 | — | — | — | — |
| EtOH | 48.0 | 48.0 | 48.0 | 48.0 | 45.0 | 45.0 | 45.0 | 45.0 |
| CHG | 5.99 | 5.99 | 5.99 | 5.99 | 1.58 | 3.15 | 6.30 | 12.60 |
| Water | 4.69 | 4.09 | 4.99 | 4.39 | 13.42 | 11.85 | 8.70 | 2.40 |
| Log Reduction | 2.6 | 2.3 | 2.3 | 2.1 | 1.3 | 2.9 | 4.1 | 4.1 |
| Tack | No | No | No | No | — | — | — | — |
| Flexible on skin after drying | Yes | Yes | Yes | Yes | — | — | — | — |
| Feel on skin | Smooth | Smooth | Smooth | Smooth | — | — | — | — |
| Rubs off? | No | No | No | No | — | — | — | — |

TABLE 3

| Components | C1 | Example 5 | C2 | C3 | Example 6 |
|---|---|---|---|---|---|
| Ethocel 100 | 2.1 | 2.1 | 2.1 | — | 2.1 |
| DIPS | — | 2.1 | 2.1 | 2.1 | — |
| DIPA | — | — | — | — | 2.1 |
| EtOH | 50.28 | 50.28 | 50.28 | 50.28 | 50.28 |
| CHG | 3.15 | 3.15 | — | 3.15 | 3.15 |
| Water | 4.47 | 2.37 | 5.52 | 4.47 | 2.37 |
| Log Reduction | 0.6 | 1.9 | 0.1 | 1.8 | 2.3 |
| Tack | No | No | No | No | No |
| Flexible on skin after drying | No | Yes | Yes | Yes | Yes |
| Feel on skin | Stiff, tight | Smooth | Smooth | Smooth | Smooth |
| Rubs off? | No | No | No | No | No |

Examples 7-12

The Examples shown in Table 4 were prepared by first mixing IPA with PVP and Ethocel and heating in an oven at 50° C. and mixing until dissolved. Next Myristyl alcohol was added and heated at 50° C. until dissolved. Separately, FD&C Blue 1 dye was added to water and dissolved. Glycerol and the respective ester were added to the alcohol solution and mixed. The water solution was then added to the alcohol solution, and mixed. Finally, CHG was added and the formulation was further mixed. The components are in units of grams unless otherwise noted. The Examples were tested according to the Skin Adhesion Test Protocol, described above.

TABLE 4

| Components | Control | Ex. 7 | Ex. 8 | Ex. 9 | Ex. 10 | Ex. 11 | Ex. 12 |
|---|---|---|---|---|---|---|---|
| Ethocel 100 | — | 0.8 | 0.8 | 0.8 | 0.8 | 0.8 | 0.8 |
| Glycerol | — | 0.4 | 0.4 | 0.4 | 0.4 | 0.4 | 0.4 |
| PVP | — | 0.2 | 0.2 | 0.2 | 0.2 | 0.2 | 0.2 |
| IPA | 64.5 | 64.5 | 64.5 | 64.5 | 64.5 | 64.5 | 64.5 |
| Ester | None | TEC | DBS | TEC | DBS | TEC | DBS |
| Ester Amount | — | 5.0 | 0.75 | 0.75 | 0.75 | 0.75 | 0.75 |
| Myristyl OH | — | — | — | — | 5.0 | 5.0 | 2.5 |
| CHG | 12.23 | 12.23 | 12.23 | 12.23 | 12.23 | 12.23 | 12.23 |
| Water | 23.26 | 16.86 | 21.11 | 21.11 | 16.11 | 16.11 | 18.61 |
| FD&C Blue 1 | 0.01 | 0.01 | 0.01 | 0.01 | 0.01 | 0.01 | 0.01 |
| Ave. Peel force (grams/inch) | 141.75 | 105.95 | 109.75 | 147.44 | 187.52 | 197.12 | 212.50 |
| Ave. Peel force (grams/cm) | 55.8 | 41.7 | 43.2 | 58.1 | 73.8 | 77.6 | 83.7 |

Comparative Examples C4 and C5

Comparative Examples C4-C5 were prepared by first dissolving the fatty alcohol in 200 proof Ethanol (EtOH). After the fatty alcohol was dissolved, water and the remaining components were added followed finally by adding CHG to obtain the final formulations whose compositions are shown in Table 5, below. These formulations were tested according to the Direct Inoculation Filter Assay described above. The amounts of the components in Table 5 are in grams unless otherwise noted. The total weight of each prepared Example was 60 grams.

TABLE 5

| Components | C4 | C5 |
|---|---|---|
| TBC as % of Total | 3.0% | 6.0% |
| TBC | 1.8 | 3.6 |
| EtOH | 45.60 | 44.16 |
| CHG | 6.30 | 6.30 |
| Water | 6.30 | 5.94 |
| Total Wt. | 60.0 | 60.0 |
| Log Reduction | 5.3 | 5.3 |

Comparative Examples C6-C10

Comparative Examples C6-C10 were prepared in a similar manner to Examples 1-4, above. These Examples are shown in Table 6, below, with all components listed in units of percent weight/weight (% w/w). Each formulation was evaluated for skin feel by placing about 0.5 g of the formulation on a forearm and allowing the formulation to dry for about 90 seconds followed by evaluation of the treated skin with a clean finger. The results are also shown in Table 6, below.

TABLE 6

| Components | C6 | C7 | C8 | C9 | C10 |
|---|---|---|---|---|---|
| EtOH | 80 | 80 | 80 | 80 | 80 |
| CHG | 1.9 | 1.9 | 1.9 | 1.9 | 1.9 |
| Glycerin | 0.2 | 0.2 | 0.2 | 0.2 | 0.2 |
| DIPS | — | 1 | 2 | 0.5 | 1.5 |
| Water | 17.9 | 16.9 | 15.9 | 17.4 | 16.4 |
| Feel Described | Slight stickiness | Slight tack | Oily, slippery | Dry | Slight tack |
| Acceptable Feel | No | No | No | Yes | No |

Comparative Examples C11-C14

Comparative Examples C11-C14 were prepared by the same method as Comparative Examples C6-C10, but on a separate occasion. These Examples and a Control are shown in Table 7, below, with all components listed in units of percent weight/weight (% w/w). These formulations were tested according to the Direct Inoculation Filter Assay described above and their results are shown in Tables 7, below.

TABLE 7

| Components | Control | C11 | C12 | C13 | C14 |
|---|---|---|---|---|---|
| EtOH | 80 | 80 | 80 | 80 | 80 |
| CHG | 1.9 | 1.9 | 1.9 | 1.9 | 1.9 |
| Glycerin | 0.2 | 0.2 | 0.2 | 0.2 | 0.2 |
| DIPS | — | 1 | 2 | 0.5 | 1.5 |
| Water | 17.9 | 16.9 | 15.9 | 17.4 | 16.4 |
| Log Reduction | 0.8 | 1.0 | 0.9 | 1.3 | 1.1 |

Examples 13-17

Examples 13-17 were made by first preparing a polymer premix of Ethocel, Glycerol, PVP and IPA. The remaining components were then added and stirred, with water and CHG added last. The final formulations were stirred for 2 minutes to ensure thorough mixing. The prepared Examples were evaluated according to the Skin Panel Evaluation procedure described above. The components and results for Examples 13-17 and a Control are presented in Table 8, below.

Bacterial counts were converted to $\log_{10}$ CFU/cm$^2$ before analysis. Counts of less than 1 CFU/cm$^2$ were treated as 1 CFU/cm$^2$ such that the log transformation was zero. Log reductions were calculated by subtracting the post treatment log count from the baseline log count from the same area of the back. The baseline CFU counts averaged 3.1 logs.

TABLE 8

| Components | Ex. 13 | Ex. 14 | Ex. 15 | Ex. 16 | Ex. 17 | Control |
|---|---|---|---|---|---|---|
| Ethocel 100 | 1.12 | 1.12 | 1.12 | 1.12 | 1.12 | — |
| Glycerol | 0.56 | 0.56 | 0.56 | 0.56 | 0.56 | — |
| PVP | 0.28 | 0.28 | 0.28 | 0.28 | 0.28 | — |
| IPA | 90.3 | 90.3 | 90.3 | 90.3 | 90.3 | 90.3 |
| Acetone | — | — | — | — | 14 | — |
| Myristyl OH | 3.5 | 4.2 | 2.8 | 3.15 | 3.5 | — |
| ATEC | — | — | — | — | 0.35 | — |
| ATBC | — | 4.2 | — | 6.3 | 0.35 | — |
| TBC | — | — | — | — | 2.8 | — |
| DBS | 5.32 | — | — | — | — | — |
| Permethyl 97A | — | — | 2.8 | — | 3.5 | — |
| Permethyl 99A | — | — | — | 2.1 | — | — |
| Water | 21.77 | 22.19 | 24.99 | 19.04 | 7.59 | 32.55 |
| FD&C Blue 1 | 0.035 | 0.035 | 0.035 | 0.035 | 0.035 | 0.035 |
| CHG | 17.12 | 17.12 | 17.12 | 17.12 | 17.12 | 17.12 |
| Total wt. grams | 140 | 140 | 140 | 140 | 141.5 | 140 |
| Log Red | 2.3 | 2.1 | 1.9 | 2.1 | 2.3 | 1.5 |

Various modifications and alterations of the present invention will be apparent to those skilled in the art without departing from the scope and spirit of the present invention. The Examples described in this application are illustrative of the possibilities of varying the type, quantity and ratio of composition as well as the methods for making formulations of the present invention. The complete disclosures of all patents, patent applications, and publications recited herein are incorporated by reference, as if individually incorporated by reference.

What is claimed is:

1. An antimicrobial composition comprising:
    a) a $C_2$-$C_5$ lower alcohol present in an amount of at least 35 wt-%;
    b) a hydrophobic polymer soluble or dispersible in the lower alcohol, wherein the hydrophobic polymer has a solubility in water of less than 1% at 23° C., and wherein the hydrophobic polymer is present in the composition in an amount of at least 2 wt-% based on the total weight of the antimicrobial composition;
    c) an emollient ester selected from the group consisting of diesters of bibasic acids, diesters of diols, triesters of citric acid, triesters of triols, and combinations thereof; and
    d) a cationic antimicrobial agent;
    wherein the antimicrobial composition is free of surfactants with an HLB greater than 6;
    wherein the antimicrobial composition is essentially free of hydrophilic polymers, and
    wherein hydrophilic includes water soluble and water swellable and refers to a material that will dissolve, solubilize, disperse or otherwise suspend in water at a temperature of 23° C. in an amount of at least 7% by weight, based on the total weight of the hydrophilic material in the water.

2. The antimicrobial composition of claim 1, wherein the hydrophobic polymer is soluble in the lower alcohol.

3. The antimicrobial composition of claim 1, wherein the hydrophobic polymer is soluble in the lower alcohol and selected from the group consisting of acrylates and its derivatives, cellulose and its derivatives, n-vinyl lactam copolymers and vinyl copolymers, and combinations of two or more of the foregoing.

4. The antimicrobial composition of claim 3, wherein the antimicrobial composition when dried is resistant to water.

5. A nonvolatile antimicrobial composition comprising
    (a) a hydrophobic polymer, wherein the hydrophobic polymer has a solubility in water of less than 1% at 23° C.; and
    (b) a cationic antimicrobial agent;
    (c) an emollient ester selected from the group consisting of diesters of bibasic acids, triesters of citric acid, diesters of diols, triesters of triols, and combinations thereof;
    wherein the antimicrobial composition is essentially free of hydrophilic polymers,
    wherein hydrophilic includes water soluble and water swellable and refers to a material that will dissolve, solubilize, disperse or otherwise suspend in water at a temperature of 23° C. in an amount of at least 7% by weight, based on the total weight of the hydrophilic material in the water
    wherein the antimicrobial composition when dried is resistant to water and free of surfactants.

6. The antimicrobial composition of claim 1, wherein the antimicrobial composition is free of surfactants.

7. The antimicrobial composition of claim 1, further comprising a fatty component containing one or more free hydroxyl groups selected from the group consisting of $C_{12}$-$C_{21}$ fatty alcohols, $C_{12}$-$C_{21}$ fatty ethers, $C_{12}$-$C_{21}$ fatty amides, and combinations of all of the foregoing.

8. The antimicrobial composition of claim 1, wherein the emollient ester is soluble in the lower alcohol.

9. The antimicrobial composition of claim 1, wherein the cationic antimicrobial agent is selected from the group consisting of biguanides and bisbiguanides; polymeric quaternary ammonium compounds; small molecule quaternary ammonium compounds; and compatible combinations thereof.

10. The antimicrobial composition of claim 1, wherein the emollient esters are selected from the group consisting of dibutyl adipate, diisopropyl adipate, diisobutyl adipate, dihexyl adipate, diisopropyl sebacate, dibutyl sebacate, tributyl citrate, diesters of butanediol and hexanediol, propylene glycol dicaprylate, and combinations thereof.

11. A method of improving the wet adhesion of medical adhesive article, comprising applying a composition comprising:
   a) a $C_2$-$C_5$ lower alcohol present in an amount of at least 35 wt-%;
   b) a hydrophobic polymer soluble or dispersible in the lower alcohol, wherein the hydrophobic polymer has a solubility in water of less than 1% at 23° C., and wherein the hydrophobic polymer is present in the composition in an amount of at least 2 wt-% based on the total weight of the antimicrobial composition;
   c) an emollient ester selected from the group consisting of diesters of bibasic acids, diesters of diols, triesters of citric acid, triesters of triols, and combinations thereof; and
   d) a cationic antimicrobial agent;
   wherein the antimicrobial composition is free of surfactants with an HLB greater than 6;
   wherein the antimicrobial composition is essentially free of hydrophilic polymers,
   wherein hydrophilic includes water soluble and water swellable and refers to a material that will dissolve, solubilize, disperse or otherwise suspend in water at a temperature of 23° C. in an amount of at least 7% by weight, based on the total weight of the hydrophilic material in the water; and
   applying a medical adhesive article over the composition;
   wherein the medical adhesive article has improved adhesion to skin as measured by the Wet Skin Adhesion test.

12. A method of preventing or treating a skin condition of a mammal, the method comprising the step of applying the antimicrobial compositions of claim 1 to skin.

13. A method of preventing surgical site or catheter site infections, the method comprising the step of applying the antimicrobial compositions of claim 1 prior to surgery or catheterization.

14. The antimicrobial composition of claim 4, wherein the cationic antimicrobial agent is selected from the group consisting of biguanides and bisbiguanides; polymeric quaternary ammonium compounds; small molecule quaternary ammonium compounds; and compatible combinations thereof.

15. The antimicrobial composition of claim 5, wherein the cationic antimicrobial agent is selected from the group consisting of biguanides and bisbiguanides; polymeric quaternary ammonium compounds; small molecule quaternary ammonium compounds; and compatible combinations thereof.

16. The antimicrobial composition of claim 4, further comprising a fatty component containing one or more free hydroxyl groups selected from the group consisting of $C_{12}$-$C_{21}$ fatty alcohols, $C_{12}$-$C_{21}$ fatty ethers, $C_{12}$-$C_{21}$ fatty amides, and combinations of all of the foregoing.

17. The antimicrobial composition of claim 5, further comprising a fatty component containing one or more free hydroxyl groups selected from the group consisting of $C_{12}$-$C_{21}$ fatty alcohols, $C_{12}$-$C_{21}$ fatty ethers, $C_{12}$-$C_{21}$ fatty amides, and combinations of all of the foregoing.

18. The antimicrobial composition of claim 1, wherein the hydrophobic polymer is a copolymer comprising (i) a monomeric acrylic or methacrylic acid ester of an alkyl alcohol having from 2 to about 14 carbon atoms and containing a single hydroxyl, (ii) a monomeric methacrylic acid ester of an alkyl alcohol having from 1 to 6 carbon atoms and containing a single hydroxyl, and (iii) an N-vinyl lactam.

* * * * *